United States Patent [19]

Blache et al.

[11] Patent Number: 5,523,322
[45] Date of Patent: Jun. 4, 1996

[54] METHOD FOR INHIBITING BLOOD-PLATELET AGGREGRATION WITH β-NAPHTHOQUINONE COMPOUNDS

[75] Inventors: Denis Blache, Chevigny Saint Sauveur; Christian Bloy, Paris; Bernard Hercelin, Clermont, all of France

[73] Assignee: Roussel UCLAF, France

[21] Appl. No.: 269,649

[22] Filed: Jun. 30, 1994

[30] Foreign Application Priority Data

Jul. 2, 1993 [FR] France .................. 93 08112

[51] Int. Cl.⁶ .................. A61K 31/27; A61K 31/175; A61K 31/13; A61K 31/135
[52] U.S. Cl. .................. 514/481; 514/590; 514/645; 514/646
[58] Field of Search .................. 552/292; 514/590, 514/645, 646, 481

[56] References Cited

FOREIGN PATENT DOCUMENTS 924M  1/1963  France .

OTHER PUBLICATIONS

Bressolle et al., "Pharmacokinetics of naftazone in dogs", Framaco, Ed. Prat, (1985). vol. 40, No. 6, pp. 187–198. (enclosed abstract).

La Gazette Medicale, Ploin, Michel., vol. (20) Mar. 27, 1993 p. 38.

Agressologie, vol. (12), pp. 25–30, Laborit et al., "Effects de la mono–semicarbazone de la β–naphtoquinone hemorragique" (1971).

Primary Examiner—Kevin E. Weddington
Attorney, Agent, or Firm—Bierman & Muserlian

[57] ABSTRACT

A method of inhibiting blood-platelet aggregation in warm-blooded animals comprising administering to warm-blooded animals a blood-platelet aggregation inhibiting effective amount of a compound selected from the group consisting of a compound of the formula

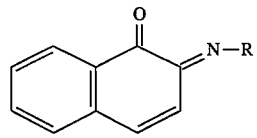

wherein R is selected from the group consisting of —NH—CO—NH$_2$, —NH—CO—CH$_3$, —OH and their non-toxic, pharmaceutically acceptable acid addition salts.

5 Claims, No Drawings

METHOD FOR INHIBITING BLOOD-PLATELET AGGREGRATION WITH β-NAPHTHOQUINONE COMPOUNDS

French BSM patent No. 924 M describes the use as medicaments of β-naphthoquinone derivatives due to their having hemostatic properties and vitamin properties. It is known that blood-platelets interact with the coagulation factors and the components of the vascular wall to play an essential and favorable rôle in the maintenance of vascular integrity, in hemostasis and, on the other hand an unfavorable rôle, in the initiation of thromboses and in the development of atherosclerosis.

OBJECTS OF THE INVENTION

It is an object of the invention to provide a novel method for inhibiting blood-platelet agglomeration in warm-blooded animals, including humans.

This and other objects and advantages of the invention will become obvious from the following detailed description.

THE INVENTION

The novel method of the invention for inhibiting blood-platelet aggregation in warm-blooded animals comprises administering to warm-blooded animals a blood-platelet aggregation inhibiting effective amount of a compound selected from the group consisting of a compound of the formula

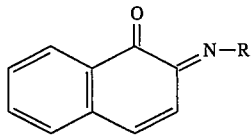

I wherein R is selected from the group consisting of —NH—CO—NH$_2$, —NH—CO—CH$_3$, —OH and their non-toxic, pharmaceutically acceptable acid addition salts.

Examples of suitable acids for the preparation of the non-toxic, pharmaceutically acceptable acid addition salts are inorganic acids such as hydrochloric acid, hydrobromic acid, hydroiodic acid, nitric acid, sulfuric acid and phosphoric acid and organic acids such as propionic acid, formic acid, benzoic acid, maleic acid, fumaric acid, succinic acid, tartaric acid, citric acid, oxalic acid, glyoxylic acid, aspartic acid, alkanesulfonic acids such as methanesulfonic acid and arylsulfonic acids such as benzenesulfonic acid.

Among the preferred compounds of the formula I are those where R is —NH—CO—NH$_2$, those wherein R is —NH—CO—CH$_3$ and those wherein R is —OH. Especially preferred is 1,2-naphthoquinone-2-semicarbazone.

The compound may be administered orally, rectally or parentally and may be in the form of tablets, dragees, gelules, capsules, suppositories and injectable solutions. Examples of suitable pharmaceutical carriers are talc, gum arabic, lactose, starch, magnesium stearate, cocoa butter, aqueous or non-aqueous vehicles, fatty substances of animal or vegetable origin, various wetting, dispersing or emulsifying agents, and preservatives.

Due to their remarkable blood-platelet aggregation inhibiting properties, the β-naphthoquinones of formula I are useful in the treatment or the prevention of arterial thrombotic complications (cerebral vascular injury, myocardial infarction) or venous thrombotic complications (phlebitis) and any vascular injury connected with atherosclerosis (in particular cerebral), in the treatment and the prevention of ischemic injuries, in the treatment of blood-platelet disorders. The usual daily dose depending on the product, the patient treated and the illness in question can be 0.01 to 1.3 mg/kg. The compounds of formula I are known and can be prepared by the process in French patent No. 2,103,504.

In the following examples, there are described several preferred embodiments to illustrate the invention. However, it is to be understood that the invention is not intended to be limited to the specific embodiments.

EXAMPLE 1

Tablets were prepared containing 10 mg of naftazone and sufficient excipient of lactose, starch, talc and magnesium stearate for a tablet of 150 mg.

EXAMPLE 2

An injectable solute was prepared containing 5 mg of naftazone and sterile aqueous excipient for a value of 2 ml.

EXAMPLE 3

8.6 g of naftazone were introduced into 200 ml of acetic anhydride and after heating for 10 hours at 140° C., then cooling, filtration is carried out. The precipitate was extracted with chloroform, followed by evaporation to dryness, taking up in ethanol, passing through activated charcoal, filtration and slow crystallization to obtain 5.1 g of product of formula I with R=—NH—CO—CH$_3$ as a yellow ocher micro-crystalline powder melting at 137°–138° C.

PHARMACOLOGICAL STUDY

I—Inhibition of blood-platelet aggregation

At present, many compounds are capable of inhibiting the blood-platelet functions but only two, aspirin and ticlopidine, have a recognized pharmacological activity: inhibition of blood-platelet aggregation. Naftazone was compared with ticlopidine and aspirin in a rat and a second time, in vitro on rat and human blood-platelets.

In vitro

The aggregation of human or rat blood-platelets isolated from their plasma and stimulated by ADP or thrombin in the presence of different concentrations of naftazone ($10^{-4}$M to $10^{-8}$M) was importantly and significantly reduced. It is approximately on the order of 70 to 20% for naftazone concentrations ranging from $10^{-4}$M to $10^{-6}$M, respectively.

Ex vivo

The effect of naftazone compared with aspirin and ticlopidine in a rat, after repeated injections of 10 mg/kg/day of each of the products, allowed an important and significant inhibition of blood-platelet aggregation induced by ADP or thrombin to be demonstrated (table 1).

| Group (n) | Plasma rich in platelets | | Washed platelets | |
| --- | --- | --- | --- | --- |
| | Thrombin | ADP | Thrombin | ADP |
| D Naftazone (6) | 32.9 ± 7.7[b] | 20.6 ± 5.6[c,d] | 24.3 ± 18.8[a,b,c,d] | 20.7 ± 19.2[a,b,c,d] |

The results of the aggregation induced by thrombin or ADP are expressed (average±S.D.) as a percentage of optical transmission. The numbers of the same column modified by the same letter are significantly different (p<0.05 at minimum)according to the Newman-Keuls test after analysis of the variance. These results show that, under the experimental conditions used, naftazone significantly inhibited blood-platelet aggregation induced by ADP or thrombin. This inhibition, revealed in vitro on human or rat blood-platelets, was confirmed in a rat. Furthermore, this effect was equivalent to that revealed with ticlopidine and aspirin under the same conditions.

Various modifications of the method of the invention may be made without departing from the spirit or scope thereof and its should be understood that the invention is intended to be limited only as defined in the appended claims.

What is claimed is:

1. A-method of inhibiting blood-platelet aggregation in warm-blooded animals comprising administering to warm-blooded animals in need thereof a blood-platelet aggregation inhibiting effective amount of a compound selected from the group consisting of a compound of the formula

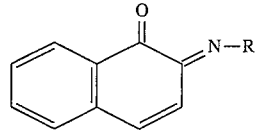

wherein R is selected from the group consisting of —NH—CO—NH$_2$, —NH—CO—CH$_3$, —OH and their non-toxic, pharmaceutically acceptable acid addition salts.

2. The method of claim 1 wherein R is —NH—CO—NH$_2$.

3. The method of claim 1 wherein R is —NH—CO—CH$_3$.

4. The method of claim 1 wherein R is —OH.

5. The method of claim 1 wherein the compound is 1,2-naphthoquinone-2-semicarbazone.

* * * * *